(12) United States Patent
Yang et al.

(10) Patent No.: US 12,258,318 B2
(45) Date of Patent: Mar. 25, 2025

(54) SYNTHESIS METHOD FOR 1-METHYL-1H-INDAZOLE-6-CARBOXYLIC ACID

(71) Applicant: ACCELA CHEMBIO CO., LTD., Shanghai (CN)

(72) Inventors: Jun Yang, Shanghai (CN); Duoqing Xue, Shanghai (CN); Yong Wu, Shanghai (CN); Lihuang Chen, Shanghai (CN); Lianhua Zhai, Shanghai (CN)

(73) Assignee: ACCELA CHEMBIO CO., LTD., Shanghai (CN)

( * ) Notice: Subject to any disclaimer, the term of this patent is extended or adjusted under 35 U.S.C. 154(b) by 718 days.

(21) Appl. No.: 17/614,473

(22) PCT Filed: Jun. 3, 2020

(86) PCT No.: PCT/CN2020/094153
§ 371 (c)(1),
(2) Date: Nov. 26, 2021

(87) PCT Pub. No.: WO2020/253533
PCT Pub. Date: Dec. 24, 2020

(65) Prior Publication Data
US 2022/0235010 A1   Jul. 28, 2022

(30) Foreign Application Priority Data
Jun. 17, 2019 (CN) .......................... 201910522457.1

(51) Int. Cl.
*C07D 231/56* (2006.01)
(52) U.S. Cl.
CPC ................. *C07D 231/56* (2013.01)
(58) Field of Classification Search
CPC .................................................. C07D 231/56
See application file for complete search history.

(56) References Cited

U.S. PATENT DOCUMENTS

2010/0324070 A1   12/2010   Dillon et al.
2015/0087829 A1   3/2015    Dahmann et al.

FOREIGN PATENT DOCUMENTS

| CN | 1562976 A | 1/2005 | | |
|---|---|---|---|---|
| CN | 101541809 A | 9/2009 | | |
| CN | 103787978 A | 5/2014 | | |
| CN | 105198813 A | 12/2015 | | |
| CN | 110128347 A | 8/2019 | | |
| EP | 1484321 A1 | 12/2004 | | |
| WO | WO-2008065508 A1 | * | 6/2008 | ......... C07D 491/107 |
| WO | WO-2014089364 A1 | * | 6/2014 | ............. A61K 31/44 |

OTHER PUBLICATIONS

A. Schoenberg, I. Bartoletti, and R. F. Heck "Palladium-catalyzed carboalkoxylation of aryl, benzyl, and vinylic halides" The Journal of Organic Chemistry 1974 39 (23), 3318-3326.*
Batt "Disubstituted Indazoles as Potent Antagonists of the Integrin avb3" Journal of Medicinal Chemistry, 2000, 43 (1), 41-58.*
Freeman-Cook "Maximizing Lipophilic Efficiency: The Use of Free-Wilson Analysis in the Design of Inhibitors of Acetyl-CoA Carboxylase" Journal of Medicinal Chemistry, 2012, 55(2), 935-942.*
J.A. Pfefferkoma, et al., "The Design and synthesis of indazole and pyrazolopyridine based glucokinase activators for the treatment of Tye 2 diabetes mellitus", Bioorganic & medicinal Chemistry Letters, vol. 22, No. 23, Dec. 1, 2012 (Dec. 1, 2012), pp. 7100-7105.
International Search Report of PCT Application No. PCT/CN2020/094153.
Lee, Esther C.Y., et al.; "Optimization of amide-based EP3 receptor antagonists," Bioorganic & Medicinal Chemistry Letters 26 (Apr. 9, 2016) 2670-2675 (5 pages).
Office Action for Chinese Application No. CN201910522457.1 dated Aug. 30, 2022 (9 pages).

* cited by examiner

*Primary Examiner* — David K O'Dell
(74) *Attorney, Agent, or Firm* — Thomas|Horstemeyer, LLP

(57) ABSTRACT

The present application provides a synthesis method for 1-methyl-1H-indazole-6-carboxylic acid. The synthesis method comprises: using 2-fluoro-4-bromobenzaldehyde and methylhydrazine as raw materials to obtain 6-bromo-1-methylindazole by means of an annulation reaction, and then performing a methyl formate reaction and a hydrolysis reaction, so as to obtain the 1-methyl-1H-indazole-6-carboxylic acid. The synthesis method provided in the present application can directly synthesize a 1-position methyl substituted indazole without isomers, thereby avoiding the problem that impurities are difficult to be removed in subsequent separation, thus improving the purity of a product. The yield of the annulation reaction can reach 85%.

13 Claims, No Drawings

SYNTHESIS METHOD FOR 1-METHYL-1H-INDAZOLE-6-CARBOXYLIC ACID

CROSS-REFERENCE TO RELATED APPLICATIONS

This application is filed pursuant to 35 USC 371 as the U.S. national stage filing of PCT Application No. PCT/CN2020/094153 entitled "SYNTHESIS METHOD FOR 1-METHYL-1H-INDAZOLE-6-CARBOXYLIC ACID" filed on Jun. 3, 2020, which claims priority benefits of Chinese Application No. 201910522457.1 filed Jun. 17, 2019. The technical disclosures of every application and publication listed in this paragraph are hereby incorporated herein by reference.

TECHNICAL FIELD

The present application belongs to the field of synthesis of pharmaceutical intermediates and relates to a synthesis method for 1-methyl-1H-indazole-6-carboxylic acid.

BACKGROUND

Currently, the synthesis of mono-substituted or poly-substituted 1-methyl-1H-indazole is reported to adopt synthesizing indazole first and then using an alkylating reagent to construct a methyl group at the 1-position, which results in the presence of a positional isomer that is difficult to remove in subsequent purification and is not conducive to the industrial scale-up production.

CN1260216A discloses a synthesis method for 1-methylindazole-3-carboxylic acid, which includes dissolving o-methylaminophenylacetonitrile in 50%-80% aqueous solution of ethanol or methanol, adding hydrochloric acid, adding aqueous solution of sodium nitrite with a concentration of 1-10 wt % to the above aqueous solution of ethanol or methanol at −5-5° C., stirring to react for 1.5-4 hours, and then adjusting a pH of the reaction solution to 2-3 to produce N-nitroso-N-methylaminophenylacetonitrile; in the presence of a weak base substance, N-nitroso-N-methylaminophenylacetonitrile is refluxed in methanol or ethanol for 2-6 hours to produce 1-methyl-3-cyanoindazole; and 1-methyl-3-cyanoindazole is refluxed and reacted in concentrated hydrochloric acid for 3-8 hours under an inert gas protection to produce 1-methylindazole-3-carboxylic acid. This method has a mild condition and is easy to operate and control, and at the same time, the problems are also avoided, such as a positional selectivity of methylation after cyclization and a harsh reaction condition that is not easy to operate and control, due to a selection of a raw material for aminomethylation, but the comprehensive yield of this method is low.

CN105198813A discloses a synthesis process for 3-methyl-1H-indazole, comprising the following steps: dropping acetophenone into a mixture of sulfuric acid and nitric acid, then adding a calcium silicate powder, keeping low temperature and stirring overnight, then adding to ice water, filtering, and obtaining 2-nitroacetophenone; using 2-nitroacetophenone, an iron powder and ammonium chloride to synthesize a white solid 2-aminoacetophenone; adding 2-aminoacetophenone to hydrochloric acid, then adding a $NaNO_2$ aqueous solution, stirring, then adding a hydrochloric acid solution of $SnCl_2 \cdot H_2O$, stirring, pouring into an ice water, filtering, adjusting the filtrate to alkalescence, filtering and drying to obtain the product. By using calcium silicate as a catalyst, significantly improved the yield of 2-nitroacetophenone, and a raw material of calcium silicate is readily available, low-costed and simple in operation and use, which is conducive to further synthesis of 2-aminoacetophenone as well as 3-methyl-1H-indazole at a later stage, and suitable for industrial large-scale synthesis of 3-methyl-1H-indazole. However, this method dose not synthesize indazole substituted with methyl at the 1-position, facing a problem of more alkylated impurities in the subsequent synthesis process, and the reaction relates to a use of sulfate acid and nitric acid, which is not conducive to industrial scale-up production.

CN103787978A discloses a synthesis method for 1-methylindazole-3-carboxylic acid. O-hydroxyacetophenone is used as a raw material in this method, reacted with hydrazine hydrate in ethanol, cyclized under an acidic condition, then oxidized with potassium permanganate, and finally subjected to an N-methylation to obtain 1-methylindazole-3-carboxylic acid. This method has the raw material which is easy to get, simple route, mild reaction condition and simple post-treatment and is suitable for industrial large-scale production, but this method suffers from the problem of more impurities after methylation, which is not conducive to the separation of the product.

Therefore, how to develop a novel method for 1-methyl-1H-indazole has important significance and value for a downstream utilization of a product with an alkylated structure at the 1-position.

SUMMARY

The summary of the subject matter described in detail herein is given below. This summary is not intended to limit the protection scope of the claims.

An object of the present application is to provide a synthesis method for 1-methyl-1H-indazole-6-carboxylic acid, so as to solve the problem in the prior art that there are isomers when using an alkylating agent to construct a methyl group at the 1-position, resulting in more impurities that are difficult to be removed and a relative low yield.

To achieve the object, the present application adopts technical solution described below.

The present application provides a synthesis method for 1-methyl-1H-indazole-6-carboxylic acid. The synthesis method comprising:

using 2-fluoro-4-bromobenzaldehyde and methylhydrazine as raw materials to obtain 6-bromo-1-methylindazole by means of an annulation reaction, and then performing a methyl formate reaction and a hydrolysis reaction, so as to obtain the 1-methyl-1H-indazole-6-carboxylicacid.

The synthesis method provided in the present application can directly synthesize a 1-position methyl substituted indazole without isomers, thereby avoiding the problem that impurities are difficult to be removed in the subsequent separation, thus improving the product purity. A yield of the annulation reaction can reach 85%, and the yield is relative high, which is not only suitable for small-scale preparation in the laboratory, but also can be directly scaled up for production, and a reaction condition is easy to operate and control, which is conducive to an actual industrial production.

Unless otherwise specified, % in the present application refers to weight %.

Optionally, a solvent of the annulation reaction is any one or a combination of at least two of N,N-dimethylacetamide, N,N-dimethylformamide, N-methylmorpholine, N-methylpyrrolidone or dimethyl sulfoxide; optionally, N,N-dimethylacetamide.

In the present application, although several commonly used solvents can make the reaction proceed properly, when N,N-dimethylacetamide is selected as the solvent for the reaction, the annulation reaction has the highest yield which can reach more than 85%. However, when dimethyl sulfoxide, N,N-dimethylformamide or the like is selected as the solvent, the reaction yield cannot achieve the best effect.

Optionally, the annulation reaction is carried out in the presence of a base.

In the present application, an addition of the base is generally processed at −5° C.-to 5° C., and then the temperature is raised to carry out the reaction.

Optionally, the base for the annulation reaction is any one or a combination of at least two of potassium carbonate, cesium carbonate, triethylamine, potassium tert-butanol or sodium ethanol; optionally, potassium carbonate.

In the present application, in the process of the annulation reaction, methylhydrazine and aldehyde rapidly react, and then the structure of indazole is formed by a ring closure in the presence of the base.

Optionally, 2-fluoro-4-bromobenzaldehyde, methylhydrazine and the base has a molar ratio of 1:(1-1.2):(1.5-2), which may be, for example, 1:1:1.5, 1:1.1:1.6, 1:1.2:1.8, 1:1.1:2 or the like.

In the present application, methylhydrazine is a 40 wt. % aqueous solution of methylhydrazine.

Optionally, the annulation reaction has a temperature of 95° C. to 105° C., which may be, for example, 95° C., 96° C., 97° C., 98° C., 99° C., 100° C., 101° C., 102° C., 103° C., 104° C., 105° C. or the like.

The synthesis method provided in the present application can achieve rapid and high yield synthesis at a lower temperature during the annulation reaction process, whereas the prior methods require a higher temperature to be processed, consuming more energy.

Optionally, the annulation reaction has a time of 35 h to 40 h, which may be, for example, 35 h, 36 h, 37 h, 38 h, 39 h, 40 h, or the like.

A post-treatment for the annulation reaction generally uses ethyl acetate and water to extract, after washing with hydrochloric acid, a saturated sodium bicarbonate solution and a saturated salt solution, a product can be obtained by crystallizing from n-heptane.

Optionally, the methyl formate reaction comprising: dissolving 6-bromo-1-methylindazoleis in methanol, and in the presence of a base and a catalyst, performing the methyl formate reaction under a carbon monoxide atmosphere to obtain methyl 1-methyl-1H-indazole-6-carboxylate.

In the present application, when the methyl formate reaction is completed, by using methyl tert-butyl ether to drip wash, filtering, then washing through hydrochloric acid, a saturated sodium bicarbonate solution and a saturated salt solution, crystallizing from n-heptane, and drying to obtain a product.

Optionally, 6-bromo-1-methylindazole, the base and the catalyst have a molar ratio of 1:(2-3):(0.02-0.5), which may be, for example, 1:2:0.02, 1:2.3:0.1. 1:2.6:0.2, 1:3:0.5 or the like.

Optionally, in the methyl formate reaction, the base is any one or a combination of at least two of triethylamine, potassium carbonate or sodium bicarbonate, optionally triethylamine.

Optionally, the catalyst is [1,1′-bis(diphenylphosphino)ferrocene]palladium(II)dichloride dichloromethane complex.

Optionally, a pressure under the carbon monoxide atmosphere is 4.5 MPa to 5.0 MPa, which may be, for example, 4.5 MPa, 4.6 MPa, 4.7 MPa, 4.8 MPa, 4.9 MPa, 5.0 MPa or the like.

Optionally, the methyl formate reaction has a temperature of 100° C. to 110° C., which may be, for example, 100° C., 101° C., 102° C., 103° C., 104° C., 105° C., 106° C., 107° C., 108° C., 109° C., 110° C. or the like.

Optionally, the methyl formate reaction has a time of 15 h to 20 h, which may be, for example, 15 h, 16 h, 17 h, 18 h, 19 h, 20 h or the like.

Optionally, the hydrolysis reaction is to hydrolyze methyl 1-methyl-1H-indazole-6-carboxylate under an alkaline condition to obtain 1-methyl-1H-indazole-6-carboxylic acid.

In the present application, after a hydrolysis under the alkaline condition, by washing with methyl tert-butyl ether, acidifying, and drying to obtain a final product 1-methyl-1H-indazole-6-carboxylic acid.

Optionally, the alkaline condition is provided by sodium hydroxide.

Optionally, methyl 1-methyl-1H-indazole-6-carboxylate and sodium hydroxide have a molar ratio of 1:0.9-1, which may be, for example, 1:0.9, 1:0.91, 1:0.92, 1:0.93, 1:0.94, 1:0.95, 1:0.96, 1:0.97, 1:0.98, 1:0.99, 1:1 or the like.

Optionally, a solvent for the hydrolysis is a mixed solution of methanol and water.

Optionally, the hydrolysis has a temperature of 20° C. to 30° C., which may be, for example, 20° C., 21° C., 22° C., 23° C., 24° C., 25° C., 26° C., 27° C., 28° C., 29° C., 30° C. or the like.

Optionally, the hydrolysis has a time of 15 h to 20 h, which may be, for example, 15 h, 16 h, 17 h, 18 h, 19 h, 20 h or the like.

Optionally, the synthesis method comprises the following steps:
(1) using 2-fluoro-4-bromobenzaldehyde and methylhydrazine as raw materials, performing the annulation reaction in the presence of a base at 95-105° C. for 35-40 h, after that, crystallizing from n-heptane to obtain 6-bromo-1-methylindazole, wherein 2-fluoro-4-bromobenzaldehyde, methylhydrazine and the base have a molar ratio of 1:(1-1.2):(1.5-2);
(2) dissolving 6-bromo-1-methyl-indazole in methanol, putting into an autoclave, and in the presence of a base and a catalyst, performing the methyl formate reaction at 100-110° C. for 15-20 h under a carbon monoxide atmosphere and a pressure of 4.5-5.0 MPa, washing with methyl tert-butyl ether after the reaction, and crystallizing from n-heptane to obtain methyl 1-methyl-1H-indazole-6-carboxylate, wherein 6-bromo-1-methyl indazole, the base and the catalyst have a molar ratio of 1:(2-3):(0.02-0.5);
(3) dissolving methyl 1-methyl-1H-indazole-6-carboxylate in a mixed solution of methanol and water, cooling to 0-10° C., adding with a base, raising the temperature to 20-30° C., and performing the hydrolysis reaction for 15-20 h to obtain 1-methyl-1H-indazole-6-carboxylic acid, wherein methyl 1-methyl-1H-indazole-6-carboxylate and the base have a molar ratio of 1:0.9-1.

In the present application, there is no particular limitation on the amount of a reaction solvent generally. Generally, as long as it can ensure that a solid can be fully dissolved to facilitate a continuous progress of the reaction, and those skilled in the art may adjust it according to an actual reaction situation.

Compared to the prior art, the present application has the following beneficial effects.

The synthesis method provided in the present application can directly synthesize 1-position methyl substituted indazole without isomers, thereby avoiding the problem that impurities are difficult to be removed in the subsequent separation, thus improving the product purity. A yield of the annulation reaction can reach 85%, and the yield is relative high, which is not only suitable for small-scale preparation in the laboratory, but also can be directly scaled up for production, and a reaction condition is easy to operate and control, which is conducive to reducing production costs and expanding the actual industrial production.

After reading and understanding the detailed description, other aspects can be understood.

DETAILED DESCRIPTION

The technical solutions of the present application will be further described below through specific embodiments. Those skilled in the art are to understand that the examples described herein are merely used for a better understanding of the present application and are not to be construed as specific limitations to the present application.

Example 1

This example provides a synthesis method for 1-methyl-1H-indazole-6-carboxylic acid.

(1) 20.0 mL of N,N-dimethylacetamide and 10.0 g (0.05 mol, 1.00 equ.) of 2-fluoro-4-bromobenzaldehyde were added into a reaction flask, cooled to 0° C., 10.2 g (0.08 mol, 1.50 equ.) of potassium carbonate was added, and then 20.0 mL of methylhydrazine (40 wt. % aqueous solution) was added dropwise. After the addition, the temperature was raised to 100° C. and reacted for 40 h, raw materials were reacted completely, and the reaction system was cooled to room temperature. Ethyl acetate and water were added for extraction, and layers were separated. An organic phase was washed separately by 2M hydrochloric acid aqueous solution, 7% sodium bicarbonate aqueous solution and saturated salt solution, and the organic phase was concentrated, crystallized from n-heptane, filtered and dried to obtain 9.0 g of 6-bromo-1-methylindazole with a yield of 85%.

$^1$H NMR (300 MHz, CDCl$_3$): δ 7.96 (1H, S), δ 7.61 (1H, S), δ 7.59 (1H, d, J=8.1 Hz), δ 7.26 (1H, d, J=8.1 Hz), δ 4.05 (3H, S).

(2) 88.0 g (0.42 mol, 1.00 equ.) of 6-bromo-1-methylindazole, 540.0 mL of methanol, 84.0 g (0.84 mol, 2.00 equ.) of triethylamine and 5.0 g of [1,1'-bis(diphenylphosphino)ferrocene]palladium(II)dichloride dichloromethane complex were added into an autoclave. After the addition, air in the autoclave was replaced with carbon monoxide. The reaction system had a pressure of 5.0 MPa, was raised to a temperature of 100° C., and reacted for 20 h. After raw materials were reacted completely, the reaction solution was cooled to room temperature and filtered. A filter cake was drip washed with a small amount of methanol. A filtrate was concentrated to 35.5 mL, then added with 250.0 mL of methyl tert-butyl ether, stirred for 4 h at room temperature and filtered. The filter cake was drip washed with 55 mL of methyl tert-butyl ether. The filtrate was washed separately by 2M hydrochloric acid aqueous solution, 7% sodium bicarbonate aqueous solution and saturated salt solution. An organic phase was concentrated followed by crystallization from n-heptane and filtration. The filter cake was dried at 45° C. for 20 h to obtain 55.9 g of methyl 1-methyl-1H-indazole-6-carboxylate with a yield of 70%.

$^1$H NMR (300 MHz, CDCl$_3$): δ 8.20 (1H, S), δ 8.05 (1H, S), δ 7.80 (1H, d, J=8.1 Hz), δ 7.78 (1H, d, J=8.1 Hz), δ 4.16 (3H, S), δ 4.00 (3H, S).

(3) 56.0 g (0.29 mol, 1.00 equ.) of methyl 1-methyl-1H-indazole-6-carboxylate, 560.0 mL of methanol and 560.0 mL of water were added into a reaction flask, cooled to 5° C., and 35.3 g (0.88 mol, 0.90 equ.) of sodium hydroxide was added. After the addition, the temperature was raised to 25° C. and reacted for 20 hours, raw materials were reacted completely, and the reaction system was concentrated to 250.0 mL and washed with 100.0 mL of methyl tert-butyl ether. An aqueous phase was adjusted to pH 2 with 2 mol/L hydrochloric acid aqueous solution and filtered. A filter cake was dried to obtain 36.8 g of 1-methyl-1H-indazole-6-carboxylic acid with a yield of 71%.

$^1$H NMR (300 MHz, CDCl$_3$): δ 13.07 (1H, S), δ 8.28 (1H, S), δ 8.16 (1H, S), δ 7.85 (1H, d, J=8.4 Hz), δ 7.70 (1H, d, J=8.4 Hz).

MS (ESI$^-$, m/z)=175.1.

Example 2

This example provides a synthesis method for 1-methyl-1H-indazole-6-carboxylic acid.

(1) 30.0 mL of N,N-dimethylacetamide and 10.0 g (0.05 mol, 1.00 equ.) of 2-fluoro-4-bromobenzaldehyde were added into a reaction flask, cooled to 5° C., 13.6 g (0.11 mol, 2 equ.) of potassium carbonate was added, and then 22.0 mL of methylhydrazine (40 wt. % aqueous solution) was added dropwise. After the addition, the temperature was raised to 105° C. and reacted for 35 h, raw materials were reacted completely, and the reaction system was cooled to room temperature. Ethyl acetate and water were added for extraction, and layers were separated. An organic phase was washed separately by 2M hydrochloric acid aqueous solution, 7% sodium bicarbonate aqueous solution and saturated salt solution, and the organic phase was concentrated, crystallized from n-heptane, filtered and dried to obtain 8.8 g of 6-bromo-1-methylindazole with a yield of 83%.

$^1$H NMR (300 MHz, CDCl$_3$): δ 7.96 (1H, S), δ 7.61 (1H, S), δ 7.59 (1H, d, J=8.1 Hz), δ 7.26 (1H, d, J=8.1 Hz), δ 4.05 (3H, S).

(2) 88.0 g (0.42 mol, 1.00 equ.) of 6-bromo-1-methylindazole, 540.0 mL of methanol, 84.0 g (0.84 mol, 2.00 equ.) of triethylamine and 4.0 g of [1,1'-bis(diphenylphosphino)ferrocene]palladium(II)dichloride dichloromethane complex were added into an autoclave. After the addition, air in the autoclave was replaced with carbon monoxide. The reaction system had a pressure of 4.5 MPa, was raised to a temperature of 100° C., and reacted for 15 h. After raw materials were reacted completely, the reaction solution was cooled to room temperature and filtered. A filter cake was drip washed with a small amount of methanol. A filtrate was concentrated to 35.5 mL, then added with 250.0 mL of methyl tert-butyl ether, stirred for 4 h at room temperature and filtered. The filter cake was drip washed with 55 mL of methyl tert-butyl ether. The filtrate was washed separately by 2M hydrochloric acid aqueous solution, 7% sodium bicarbonate aqueous solution and saturated salt solution. An organic phase was concentrated followed by crystallization from n-heptane and filtration. The filter cake was dried at 45° C. for 20 h to obtain 55.1 g of methyl 1-methyl-1H-indazole-6-carboxylate with a yield of 69%.

$^1$H NMR (300 MHz, CDCl$_3$): δ 8.20 (1H, S), δ 8.05 (1H, S), δ 7.80 (1H, d, J=8.1 Hz), δ 7.78 (1H, d, J=8.1 Hz), δ 4.16 (3H, S), δ 4.00 (3H, S).

(3) 56.0 g (0.29 mol, 1.00 equ.) of methyl 1-methyl-1H-indazole-6-carboxylate, 560.0 mL of methanol and 560.0 mL of water were added into a reaction flask, cooled to 0° C., and 35.3 g (0.88 mol, 0.90 equ.) of sodium hydroxide was added. After the addition, the temperature was raised to 30° C. and reacted for 15 hours, raw materials were reacted completely, and the reaction system was concentrated to 250.0 mL and washed with 100.0 mL of methyl tert-butyl ether. An aqueous phase was adjusted to pH 2 with 2 mol/L hydrochloric acid aqueous solution and filtered. A filter cake was dried to obtain 36.1 g of 1-methyl-1H-indazole-6-carboxylic acid with a yield of 70%.

$^1$H NMR (300 MHz, CDCl$_3$): δ 13.07 (1H, S), δ 8.28 (1H, S), δ 8.16 (1H, S), δ 7.85 (1H, d, J=8.4 Hz), δ 7.70 (1H, d, J=8.4 Hz).

MS (ESI$^-$, m/z)=175.1.

Example 3

This example provides a synthesis method for 1-methyl-1H-indazole-6-carboxylic acid.

(1) 20.0 mL of N,N-dimethylacetamide and 10.0 g (0.05 mol, 1.00 equ.) of 2-fluoro-4-bromobenzaldehyde were added into a reaction flask, cooled to −5° C., 10.2 g (0.08 mol, 1.50 equ.) of potassium carbonate was added, and then 20.0 mL of methylhydrazine (40 wt. % aqueous solution) was added dropwise. After the addition, the temperature was raised to 95° C. and reacted for 40 h, raw materials were reacted completely, and the reaction system was cooled to room temperature. Ethyl acetate and water were added for extraction, and layers were separated. An organic phase was washed separately by 2M hydrochloric acid aqueous solution, 7% sodium bicarbonate aqueous solution and saturated salt solution, and the organic phase was concentrated, crystallized from n-heptane, filtered and dried to obtain 8.9 g of 6-bromo-1-methylindazole with a yield of 84%.

$^1$H NMR (300 MHz, CDCl$_3$): δ 7.96 (1H, S), δ 7.61 (1H, S), δ 7.59 (1H, d, J=8.1 Hz), δ 7.26 (1H, d, J=8.1 Hz), δ 4.05 (3H, S).

(2) 88.0 g (0.42 mol, 1.00 equ.) of 6-bromo-1-methylindazole, 540.0 mL of methanol, 84.0 g (0.84 mol, 2.00 equ.) of triethylamine and 5.0 g of [1,1'-bis(diphenylphosphino)ferrocene]palladium(II)dichloride dichloromethane complex were added into an autoclave. After the addition, air in the autoclave was replaced with carbon monoxide. The reaction system had a pressure of 4.5 MPa, was raised to a temperature of 100° C., and reacted for 15 h. After raw materials were reacted completely, the reaction solution was cooled to room temperature and filtered. A filter cake was drip washed with a small amount of methanol. A filtrate was concentrated to 35.5 mL, then added with 250.0 mL of methyl tert-butyl ether, stirred for 4 h at room temperature and filtered. The filter cake was drip washed with 55 mL of methyl tert-butyl ether. The filtrate was washed separately by 2M hydrochloric acid aqueous solution, 7% sodium bicarbonate aqueous solution and saturated salt solution. An organic phase was concentrated followed by crystallization from n-heptane and filtration. The filter cake was dried at 45° C. for 20 h to obtain 55.5 g of methyl 1-methyl-1H-indazole-6-carboxylate with a yield of 69.5%.

$^1$H NMR (300 MHz, CDCl$_3$): δ 8.20 (1H, S), δ 8.05 (1H, S), δ 7.80 (1H, d, J=8.1 Hz), δ 7.78 (1H, d, J=8.1 Hz), δ 4.16 (3H, S), δ 4.00 (3H, S).

(3) 56.0 g (0.29 mol, 1.00 equ.) of methyl 1-methyl-1H-indazole-6-carboxylate, 560.0 mL of methanol and 560.0 mL of water were added into a reaction flask, cooled to 5° C., and 35.1 g (0.88 mol, 0.90 equ.) of sodium hydroxide was added. After the addition, the temperature was raised to 20° C. and reacted for 20 hours, raw materials were reacted completely, and the reaction system was concentrated to 250.0 mL and washed with 100.0 mL of methyl tert-butyl ether. An aqueous phase was adjusted to pH 1 with 2 mol/L hydrochloric acid aqueous solution and filtered. A filter cake was dried to obtain 36.1 g of 1-methyl-1H-indazole-6-carboxylic acid with a yield of 69%.

$^1$H NMR (300 MHz, CDCl$_3$): δ 13.07 (1H, S), δ 8.28 (1H, S), δ 8.16 (1H, S), δ 7.85 (1H, d, J=8.4 Hz), δ 7.70 (1H, d, J=8.4 Hz).

MS (ESI$^-$, m/z)=175.1.

Example 4

This example differs from Example 1 in that the solvent for the reaction in step (1) of this example was 20.0 mL of N,N-dimethylformamide. The yield of step (1) was 65%.

Example 5

This example differs from Example 1 in that the solvent for the reaction in step (1) of this example was 20.0 mL of dimethyl sulfoxide. The yield of step (1) was 70%.

Example 6

This example differs from Example 1 in that the solvent for the reaction in step (1) of this example was 20.0 mL of ethylene glycol. The yield of step (1) was 40%.

Example 7

This example differs from Example 1 in that the solvent for the reaction in step (1) of this example was 20.0 mL of N-methylpyrrolidone. The yield of step (1) was 80%.

Example 8

This example differs from Example 1 in that the base used for the reaction in step (1) of this example was triethylamine. The yield of step (1) was 60%.

Example 9

This example differs from Example 1 in that the base used for the reaction in step (1) of this example was potassium tert-butoxide. The yield of step (1) was 50%.

It can be concluded from the above examples that using N,N-dimethylacetamide in the reaction of step (1) can reach the highest yield, and the price is relative low, which is very suitable for industrial production; and the base used in step (1) is commonly used potassium carbonate, which has a higher synthesis yield and a lower price compared to other bases.

In summary, the synthesis method provided in the present application has the highest yield of the reaction by preferably using N,N-dimethylacetamide and potassium carbonate.

Example 10

This example provides a method for the production of 1-methyl-1H-indazole-6-carboxylic acid in kilogram scale-up.

(1) 3000.0 mL of N,N-dimethylacetamide and 1500.0 g (7.39 mol, 1.00 equ.) of 2-fluoro-4-bromobenzaldehyde were added into a reaction flask, cooled to 0° C., 1530.0 g (11.10 mol, 1.50 equ.) of potassium carbonate was added, and then 3000.0 mL of methylhydrazine (40 wt. % aqueous solution) was added dropwise. After the addition, the temperature was raised to 100° C. and reacted for 40 h, raw materials were reacted completely, and the reaction system was cooled to room temperature. Ethyl acetate and water were added for extraction, and layers were separated. An organic phase was washed separately by 2M hydrochloric acid aqueous solution, 7% sodium bicarbonate aqueous solution and saturated salt solution, and the organic phase was concentrated, crystallized from n-heptane and filtered. A filter cake was dried at 40° C. for 22 h to obtain 1320.0 g of 6-bromo-1-methylindazole with a yield of 85%.

$^1$H NMR (300 MHz, CDCl$_3$): δ 7.96 (1H, S), δ 7.61 (1H, S), δ 7.59 (1H, d, J=8.1 Hz), δ 7.26 (1H, d, J=8.1 Hz), δ 4.05 (3H, S).

(2) 1700.0 g (8.05 mol, 1.00 equ.) of 6-bromo-1-methylindazole, 11000.0 mL of methanol, 1630.0 g (16.10 mol, 2.00 equ.) of triethylamine and 85.0 g of [1,1'-bis(diphenylphosphino)ferrocene]palladium(II)dichloride dichloromethane complex were added into an autoclave. After the addition, air in the autoclave was replaced with carbon monoxide. The reaction system had a pressure of 5.0 MPa, was raised to a temperature of 110° C., and reacted for 20 h. After raw materials were reacted completely, the reaction solution was cooled to room temperature and filtered. A filter cake was drip washed with a small amount of methanol. A filtrate was concentrated to 3000.0 mL, then added with 21500.0 mL of methyl tert-butyl ether, stirred for 4 h at room temperature and filtered. The filter cake was drip washed with a small amount of methyl tert-butyl ether. The filtrate was washed separately by 2M hydrochloric acid aqueous solution, 7% sodium bicarbonate aqueous solution and saturated salt solution. An organic phase was concentrated followed by crystallization from n-heptane and filtration. The filter cake was dried to obtain 1500.0 g of 6-bromo-1-methylindazole with a yield of 98%.

$^1$H NMR (300 MHz, CDCl$_3$): δ 8.20 (1H, S), δ 8.05 (1H, S), δ 7.80 (1H, d, J=8.1 Hz), δ 7.78 (1H, d, J=8.1 Hz), δ 4.16 (3H, S), δ 4.00 (3H, S).

(3) 1450.0 g (7.62 mol, 1.00 equ.) of methyl 1-methyl-1H-indazole-6-carboxylate, 9600.0 mL of methanol and 96.00 mL of water were added into a reaction flask, cooled to 5° C., and 548.0 g (13.72 mol, 1.8 equ.) of sodium hydroxide was added. After the addition, the temperature was raised to 25° C. and reacted for 20 hours, raw materials were reacted completely, and the reaction system was concentrated to 10000.0-105000.0 mL and washed 3 times separately with methyl tert-butyl ether. An aqueous phase was adjusted to pH 2 with 2 mol/L hydrochloric acid aqueous solution and filtered. A filter cake was dried to obtain 895.0 g of 1-methyl-1H-indazole-6-carboxylic acid with a yield of 67%.

$^1$H NMR (300 MHz, CDCl$_3$): δ 13.07 (1H, S), δ 8.28 (1H, S), δ 8.16 (1H, S), δ 7.85 (1H, d, J=8.4 Hz), δ 7.70 (1H, d, J=8.4 Hz).

MS (ESI$^-$, m/z)=175.1.

As can be seen from the results of Example 10, the synthesis method provided in the present application can be directly scaled up for production without additional impurities and security problems during the scaling up process, and can maintain the original yield and be easily operated.

The applicant has stated that although the synthesis method for 1-methyl-1H-indazole-6-carboxylic acid in the present application are described through the examples described above, the present application is not limited to the examples described above, which means that implementation of the present application does not necessarily depend on the examples described above.

What is claimed is:

1. A synthesis method for 1-methyl-1H-indazole-6-carboxylic acid, comprising:
    subjecting 2-fluoro-4-bromobenzaldehyde and methylhydrazine as raw materials to an annulation reaction to obtain 6-bromo-1-methylindazole;
    dissolving the 6-bromo-1-methylindazole in methanol and performing a reaction under a carbon monoxide atmosphere in the presence of a first base and a catalyst to obtain methyl 1-methyl-1H-indazole-6-carboxylate; and
    subjecting the methyl 1-methyl-1H-indazole-6-carboxylate to a hydrolysis reaction to obtain the 1-methyl-1H-indazole-6-carboxylic acid;
    wherein in the annulation reaction a solvent is used, and the solvent is N,N-dimethylacetamide.

2. The synthesis method according to claim 1, wherein the annulation reaction is carried out in the presence of a second base; and the second base is any one or a combination of at least two selected from the group consisting of potassium carbonate, cesium carbonate, triethylamine, potassium tert-butoxide, and sodium ethanol.

3. The synthesis method according to claim 2, wherein the second base is potassium carbonate.

4. The synthesis method according to claim 2, wherein a molar ratio of the 2-fluoro-4-bromobenzaldehyde, the methylhydrazine and the second base is in a range of 1:(1-1.2):(1.5-2).

5. The synthesis method according to claim 1, wherein the annulation reaction is performed at a temperature of 95° C. to 105° C.; and
    the annulation reaction is performed for 35 h to 40 h.

6. The synthesis method according to claim 1, wherein a molar ratio of the 6-bromo-1-methylindazole, the first base and the catalyst is in a range of 1:(2-3):(0.02-0.5);
    the first base in the reaction is any one or a combination of at least two selected from the group consisting of triethylamine, potassium carbonate, and sodium bicarbonate;
    the catalyst is [1,1'-bis(diphenylphosphino)ferrocene]palladium(II)dichloride dichloromethane complex;
    a pressure under the carbon monoxide atmosphere is 4.5 MPa to 5.0 MPa;
    the reaction is performed at a temperature of 100° C. to 110° C.; and
    the reaction is performed for 15 h to 20 h.

7. The synthesis method according to claim 1, wherein the hydrolysis reaction is performed by hydrolyzing the methyl 1-methyl-1H-indazole-6-carboxylate under an alkaline condition to obtain the 1-methyl-1H-indazole-6-carboxylic acid.

8. The synthesis method according to claim 7, wherein the alkaline condition is provided by sodium hydroxide;
    a molar ratio of the methyl 1-methyl-1H-indazole-6-carboxylate to the sodium hydroxide is in a range of 1:0.9-1;
    a solvent for the hydrolysis reaction is a mixed solution of methanol and water;
    the hydrolysis reaction is performed at a temperature of 20° C. to 30° C.; and
    the hydrolysis reaction is performed for 15 h to 20 h.

9. The synthesis method according to claim 1, wherein the synthesis method comprises the following steps:
   (1) subjecting the 2-fluoro-4-bromobenzaldehyde and the methylhydrazine as raw materials to the annulation reaction in the presence of a second base at a temperature of 95-105° C. for 35-40 h, and after that, crystallizing from n-heptane to obtain the 6-bromo-1-methylindazole, wherein a molar ratio of the 2-fluoro-4-bromobenzaldehyde, the methylhydrazine and the second base is in a range of 1:(1-1.2):(1.5-2);
   (2) dissolving the 6-bromo-1-methyl-indazole in the methanol, putting a resulting solution into an autoclave, and performing the reaction at 100-110° C. for 15-20 h under the carbon monoxide atmosphere and a pressure of 4.5-5.0 MPa in the presence of the first base and the catalyst, washing with methyl tert-butyl ether after the reaction, and crystallizing from the n-heptane to obtain the methyl 1-methyl-1H-indazole-6-carboxylate, wherein a molar ratio of the 6-bromo-1-methyl indazole, the first base and the catalyst is in a range of 1:(2-3):(0.02-0.5); and
   (3) dissolving the methyl 1-methyl-1H-indazole-6-carboxylate in a mixed solution of methanol and water, cooling to 0-10° C., adding with a third base, heating a resulting mixture to a temperature of 20-30° C., and performing the hydrolysis reaction for 15-20 h to obtain the 1-methyl-1H-indazole-6-carboxylic acid, wherein a molar ratio of the methyl 1-methyl-1H-indazole-6-carboxylate to the third base is in a range of 1:0.9-1.

10. The synthesis method according to claim 6, wherein the first base in the reaction is the triethylamine.

11. The synthesis method according to claim 9, wherein the first base is any one or a combination of at least two selected from the group consisting of triethylamine, potassium carbonate, and sodium bicarbonate.

12. The synthesis method according to claim 9, wherein the second base is any one or a combination of at least two selected from the group consisting of potassium carbonate, cesium carbonate, triethylamine, potassium tert-butoxide, and sodium ethoxide.

13. The synthesis method according to claim 9, wherein the third base is sodium hydroxide.

* * * * *